United States Patent
Gelbman et al.

(10) Patent No.: US 10,470,659 B2
(45) Date of Patent: Nov. 12, 2019

(54) SYSTEMS, METHODS, AND COMPUTER-READABLE MEDIA FOR GENE AND GENETIC VARIANT PRIORITIZATION

(71) Applicant: FDNA INC., Tortola (VG)

(72) Inventors: Dekel Gelbman, Newton, MA (US); Yaron Gurovich, Rehovot (IL)

(73) Assignee: FDNA Inc., Tortola (VG)

( * ) Notice: Subject to any disclaimer, the term of this patent is extended or adjusted under 35 U.S.C. 154(b) by 0 days.

(21) Appl. No.: 16/041,723

(22) Filed: Jul. 20, 2018

(65) Prior Publication Data

US 2018/0353072 A1    Dec. 13, 2018

Related U.S. Application Data

(63) Continuation of application No. PCT/US2018/036754, filed on Jun. 8, 2018.

(Continued)

(51) Int. Cl.
    *G06F 15/18*     (2006.01)
    *A61B 5/00*     (2006.01)
    (Continued)

(52) U.S. Cl.
    CPC ............ *A61B 5/0013* (2013.01); *A61B 5/004* (2013.01); *A61B 5/0036* (2018.08);
    (Continued)

(58) Field of Classification Search
    CPC ........................... G06N 20/00; G01N 33/5091
    (Continued)

(56) References Cited

U.S. PATENT DOCUMENTS

| | | | |
|---|---|---|---|
| 2003/0190602 A1* | 10/2003 | Pressman | C12Q 1/6809 435/5 |
| 2011/0236903 A1* | 9/2011 | McClelland | C12Q 1/6886 435/6.14 |

(Continued)

OTHER PUBLICATIONS

Tracy Dudding-Byth & Professor Brian Lovell, "How CCTV software can help diagnose intellectual disability," *BMC Series Blog*, 2018 (3 pages).

(Continued)

*Primary Examiner* — David R Vincent
(74) *Attorney, Agent, or Firm* — Finnegan, Henderson, Farabow, Garrett & Dunner, LLP

(57) ABSTRACT

Systems, methods, and computer-readable media are disclosed for performing image processing in connection with phenotypic analysis. For example, at least one processor may be configured to receive electronic numerical information corresponding to pixels reflective of at least one external soft tissue image of an individual and access geographically dispersed genetic information stored in a database. The geographically dispersed genetic information may include numerical data that correlates anomalies in pixels in soft tissue images of a plurality of geographically dispersed individuals to specific genes or to specific genetic variants. The at least one processor may also be configured to compare the electronic numerical information for the individual with the numerical data of the geographically dispersed genetic information stored in a database, to determine at least a likelihood that the individual has a specific genetic variant, and prioritize, based on the comparison, one or more genetic variants according to likelihood of pathogenicity.

21 Claims, 8 Drawing Sheets

Related U.S. Application Data

(60) Provisional application No. 62/558,091, filed on Sep. 13, 2017, provisional application No. 62/517,110, filed on Jun. 8, 2017.

(51) Int. Cl.
| | |
|---|---|
| G06N 3/08 | (2006.01) |
| G16B 40/00 | (2019.01) |
| G16B 50/00 | (2019.01) |
| G06K 9/62 | (2006.01) |
| G06N 5/04 | (2006.01) |
| G06T 7/00 | (2017.01) |
| G06N 3/04 | (2006.01) |
| G06K 9/00 | (2006.01) |
| G06K 9/46 | (2006.01) |
| G16B 30/00 | (2019.01) |
| G16B 45/00 | (2019.01) |

(52) U.S. Cl.
CPC ........ *A61B 5/7275* (2013.01); *G06K 9/00281* (2013.01); *G06K 9/00288* (2013.01); *G06K 9/4628* (2013.01); *G06K 9/6202* (2013.01); *G06K 9/6218* (2013.01); *G06N 3/0454* (2013.01); *G06N 3/08* (2013.01); *G06N 5/046* (2013.01); *G06T 7/0012* (2013.01); *G16B 40/00* (2019.02); *G16B 50/00* (2019.02); *G06T 2207/10024* (2013.01); *G06T 2207/20081* (2013.01); *G06T 2207/20084* (2013.01); *G06T 2207/30088* (2013.01); *G06T 2207/30201* (2013.01); *G16B 30/00* (2019.02); *G16B 45/00* (2019.02)

(58) Field of Classification Search
USPC ...................................................... 706/15, 45
See application file for complete search history.

(56) References Cited

U.S. PATENT DOCUMENTS

| | | | | |
|---|---|---|---|---|
| 2012/0207754 A1* | 8/2012 | Giacalone | ............ | C07K 14/195 424/134.1 |
| 2014/0126802 A1* | 5/2014 | Adiga | ................ | G06K 9/00147 382/133 |
| 2018/0057888 A1* | 3/2018 | Boothman | ........... | G01N 33/574 |

OTHER PUBLICATIONS

Tracy Dudding-Byth et al., "Computer face-matching technology using two-dimensional photographs accurately matches the facial gestalt of unrelated individuals with the same syndromic form of intellectual disability," *BMC Biotechnology*, vol. 17, No. 90, 2017 (9 pages).
Yaniv Taigman et al., "Deepface: Closing the gap to human-level performance in face verification," *Proceedings of the IEEE Conference on Computer Vision and Pattern Recognition*, Columbus, OH, 2014 (8 pages).
Yaniv Taigman et al., "Web-scale training for face identification," *Proceedings of the IEEE Conference on Computer Vision and Pattern Recognition*, Boston, MA, 2015 (9 pages).
Sergey Ioffe and Christian Szegedy, "Batch normalization: Accelerating deep network training by reducing internal covariate shift," in *ICML '15 Proceedings of the 32nd International Conference on International Conference on Machine Learning*, Lille, France, 2015 (9 pages).
Aravindh Mahendran and Andrea Vedaldi, "Understanding deep image representations by inverting them," *Proceedings of the IEEE Conference on Computer Vision and Pattern Recognition*, Boston, MA, 2015 (9 pages).
Alex Krizhevsky et al., "Imagenet classification with deep convolutional neural networks," *Advances in neural information processing systems*, Lake Tahoe, NV, 2012 (9 pages).
P. A. Baird et al., "Genetic disorders in children and young adults: a population study," *American journal of human genetics*, vol. 42, No. 5, 1988 (17 pages).
T. Hart and P. Hart, "Genetic studies of craniofacial anomalies: clinical implications and applications," *Orthodontics & craniofacial research*, vol. 12, No. 3, pp. 212-220, 2009 (9 pages).
Q. Ferry et al., "Diagnostically relevant facial gestalt information from ordinary photos," *Elife*, vol. 3, p. e02020, 2014 (22 pages).
L. Basel-Vanagaite et al., "Recognition of the cornelia de lange syndrome phenotype with facial dysmorphology novel analysis," *Clinical genetics*, vol. 89, No. 5, pp. 557-563, 2016 (7 pages).
M. C. E. Rai et al., "Using facial images for the diagnosis of genetic syndromes: A survey," in *International Conference on Communications, Signal Processing, and their Applications (ICCSPA)*, Sharjah, United Arab Emirates 2015 (6 pages).
O. Russakovsky et al., "ImageNet Large Scale Visual Recognition Challenge," *International Journal of Computer Vision (IJCV)*, vol. 115, No. 3, pp. 211-252, 2015 (42 pages).
T.-Y. Lin et al., "Microsoft coco: Common objects in context," in *European conference on computer vision*, pp. 740-755, 2014 (16 pages).
G. B. Huang et al., "Labeled faces in the wild: A database for studying face recognition in unconstrained environments," Tech. Rep. 07-49, University of Massachusetts, Amherst, MA, 2007 (14 pages).
O. M. Parkhi et al., "Deep face recognition," in *BMVC*, vol. 1, 2015 (12 pages).
D. Yi et al., "Learning face representation from scratch," arXiv, 2014, available at https://arxiv.org/abs/1411.7923 (9 pages).
F. Schroff et al., "Facenet: A unified embedding for face recognition and clustering," in *Proceedings of the IEEE Conference on Computer Vision and Pattern Recognition*, Boston, MA, 2015 (9 pages).
J. Liu et al., "Targeting ultimate accuracy: Face recognition via deep embedding," arXiv, 2015, available at https://arxiv.org/abs/1506.07310 (5 pages).
G. Levi and T. Hassner, "Age and gender classification using convolutional neural networks," in *Proceedings of the IEEE Conference on Computer Vision and Pattern Recognition Workshops*, Boston, MA, 2015 (9 pages).
Z. Liu et al., "Deep learning face attributes in the wild," in *Proceedings of the IEEE International Conference on Computer Vision*, Santiago, Chile, 2015 (9 pages).
H. Ding et al., "Facenet2expnet: Regularizing a deep face recognition net for expression recognition," arXiv, 2016, available at https://arxiv.org/abs/1609.06591 (8 pages).
P. Shukla et al., "A deep learning frame-work for recognizing developmental disorders," in *2017 IEEE Winter Conference on Applications of Computer Vision (WACV)*, Santa Rosa, CA, 2017 (10 pages).
S. Saraydemir et al., "Down syndrome diagnosis based on gabor wavelet transform," *Journal of medical systems*, vol. 36, No. 5, pp. 3205-3213, 2012 (9 pages).
K. Burcin and N. V. Vasif, "Down syndrome recognition using local binary patterns and statistical evaluation of the system," *Expert Systems with Applications*, vol. 38, No. 7, pp. 8690-8695, 2011 (6 pages).
Q. Zhao et al., "Digital facial dysmorphology for genetic screening: hierarchical constrained local model using ica," *Medical image analysis*, vol. 18, No. 5, pp. 699-710, 2014 (12 pages).
P. Kruszka et al., "Down syndrome in diverse populations," *American Journal of Medical Genetics Part A*, vol. 173, No. 1, pp. 42-53, 2017 (12 pages).
P. Kruszka et al., "22q11. 2 deletion syndrome in diverse populations," *American Journal of Medical Genetics Part A*, vol. 173, No. 4, pp. 879-888, 2017 (19 pages).
Q. Zhao et al., "Ensemble learning for the detection of facial dysmorphology," in *Engineering in Medicine and Biology Society (EMBC), 2014 36th Annual International Conference of the IEEE*, Chicago, IL, 2014 (4 pages).

(56) References Cited

OTHER PUBLICATIONS

T. Liehr et al., "Next generation phenotyping in emanuel and pallister killian syndrome using computer-aided facial dysmorphology analysis of 2d photos," *Clinical Genetics*, vol. 93, pp. 378-381, 2017 (4 pages).
J. J. Cerrolaza et al., "Identification of dysmorphic syndromes using landmark-specific local texture descriptors," in *2016 IEEE 13th International Symposium on Biomedical Imaging (ISBI)*, Prague, Czech Republic, 2016 (4 pages).
K. Kuru et al., "Biomedical visual data analysis to build an intelligent diagnostic decision support system in medical genetics," *Artificial intelligence in medicine*, vol. 62, No. 2, pp. 105-118, 2014 (14 pages).
H. S. Loos et al., "Computer-based recognition of dysmorphic faces," *European Journal of Human Genetics*, vol. 11, No. 8, pp. 555-560, 2003 (6 pages).
S. Boehringer et al., "Automated syndrome detection in a set of clinical facial photographs," *American Journal of Medical Genetics Part A*, vol. 155, No. 9, pp. 2161-2169, 2011 (9 pages).
S. Boehringer et al., "Syndrome identification based on 2d analysis software," *European Journal of Human Genetics*, vol. 14, No. 10, pp. 1082-1089, 2006 (8 pages).
P. Viola and M. Jones, "Rapid object detection using a boosted cascade of simple features," in *Proceedings of the 2001 IEEE Computer Society Conference on Computer Vision and Pattern Recognition*, Kauai, HI, 2001 (8 pages).
M. Everingham et al., "Taking the bite out of automated naming of characters in tv video," *Image and Vision Computing*, vol. 27, No. 5, pp. 545-559, 2009 (15 pages).
X. Zhu and D. Ramanan, "Face detection, pose estimation, and landmark localization in the wild," in *2012 IEEE Conference on Computer Vision and Pattern Recognition (CVPR)*, Providence, RI, 2012 (8 pages).
L. Karlinsky and S. Ullman, "Using linking features in learning nonparametric part models," *Computer Vision—ECCV 2012*, Part III, pp. 326-339, 2012 (14 pages).
M. A. Turk and A. P. Pentland, "Face recognition using eigenfaces," in *Proceedings CVPR'91, IEEE Computer Society Conference on Computer Vision and Pattern Recognition*, pp. 586-591, 1991 (6 pages).
P. N. Belhumeur et al., "Eigenfaces vs. fisherfaces: Recognition using class specific linear projection," *IEEE Transactions on pattern analysis and machine intelligence*, vol. 19, No. 7, pp. 711-720, 1997 (10 pages).
D. G. Lowe, "Distinctive image features from scale-invariant keypoints," *International journal of computer vision*, vol. 60, No. 2, pp. 91-110, 2004 (20 pages).
T. Ahonen et al., "Face description with local binary patterns: Application to face recognition," *IEEE transactions on pattern analysis and machine intelligence*, vol. 28, No. 12, pp. 2037-2041, 2006 (5 pages).
G. J. Edwards et al., "Face recognition using active appearance models," in *European conference on computer vision*, pp. 581-595, 1998 (15 pages).
A. Krizhevsky et al., "Imagenet classification with deep convolutional neural networks," in *Communications of the ACM*, vol. 60, No. 6, pp. 84-90, 2017 (7 pages).
C. Cortes and V. Vapnik, "Support vector machine," *Machine learning*, vol. 20, No. 3, pp. 273-297, 1995 (25 pages).
H. Li et al., "A convolutional neural network cascade for face detection," in *Proceedings of the IEEE Conference on Computer Vision and Pattern Recognition*, Boston, MA, 2015 (10 pages).
Y. Gurovich et al., "Quality scores for deep regression systems," in *2016 IEEE International Conference on Image Processing (ICIP)*, Phoenix, AZ, 2016 (5 pages).
G. Huang et al., "Learning to align from scratch," in *Advances in Neural Information Processing Systems*, 2012 (9 pages).
J. Yosinski et al., "How transferable are features in deep neural networks?," in *Advances in neural information processing systems*, vol. 27, 2014 (14 pages).
E. Zhou et al., "Naive-deep face recognition: Touching the limit of lfw benchmark or not?," arXiv, 2015, available at https://arxiv.org/abs/1501.04690 (5 pages).
K. He et al., "Delving deep into rectifiers: Surpassing human-level performance on imagenet classification," in *Proceedings of the IEEE international conference on computer vision*, Santiago, Chile, 2015 (9 pages).
D. Kingma and J. Ba, "Adam: A method for stochastic optimization," *3rd International Conference for Learning Representations*, San Diego, CA, 2015 (15 pages).
X. Glorot and Y. Bengio, "Understanding the difficulty of training deep feedforward neural networks," In *Proceedings of the Thirteenth International Conference on Artificial Intelligence and Statistics*, pp. 249-256, 2010 (8 pages).
S. Rohatgi et al., "Facial diagnosis of mild and variant cdls: Insights from a dysmorphologist survey," *American Journal of Medical Genetics Part A*, vol. 152, No. 7, pp. 1641-1653, 2010 (13 pages).
S. R. Braddock et al., "35th annual david w smith workshop on malformations and morphogenesis: Abstracts of the 2014 annual meeting," *American Journal of Medical Genetics Part A*, vol. 167, No. 8, pp. 1685-1740, 2015 (56 pages).
J. E. Allanson et al., "The face of noonan syndrome: Does phenotype predict genotype," American journal of medical genetics Part A, vol. 152, No. 8, pp. 1960-1966, 2010 (7 pages).
E. Y. Gulec et al., "Novel mutations in ptpn1 1 gene in two girls with noonan syndrome phenotype," International journal of cardiology, vol. 186, pp. 13-15, 2015 (3 pages).
M. Zenker et al., "Sos1 is the second most common noonan gene but plays no major role in cardio-facio-cutaneous syndrome," *Journal of medical genetics*, vol. 44, No. 10, pp. 651-656, 2007 (6 pages).
C. Rusu et al., "Genotype—phenotype correlations in noonan syndrome.," *Acta Endocrinologica*, vol. 10, No. 3, pp. 467-476, 2014 (14 pages).
H. Cave et al., "Mutations in rit1 cause noonan syndrome with possible juvenile myelomonocytic leukemia but are not involved in acute lymphoblastic leukemia," *European journal of human genetics*, vol. 24, No. 8, pp. 1124-1131, 2016 (8 pages).
K. Kouz et al., "Genotype and phenotype in patients with noonan syndrome and a rit1 mutation," *Genetics in Medicine*, vol. 18, No. 12, pp. 1226-1234, 2016 (9 pages).

\* cited by examiner

SYSTEMS, METHODS, AND COMPUTER-READABLE MEDIA FOR GENE AND GENETIC VARIANT PRIORITIZATION

RELATED APPLICATIONS

This application is a continuation of PCT International Application No. PCT/US2018/036754, filed Jun. 8, 2018, which claims the benefit of priority to U.S. Provisional Application No. 62/517,110, filed Jun. 8, 2017, and to U.S. Provisional Application No. 62/558,091, filed Sep. 13, 2017, which are incorporated herein by reference in their entireties.

TECHNICAL FIELD

The present disclosure relates to the field of image analysis and machine learning. For example, systems, methods, and computer-readable media are disclosed for matching patients with a common disease using phenotypic analysis. In addition, systems, methods, and computer-readable media are disclosed for performing gene or genetic variant prioritization in connection with phenotypic analysis.

BACKGROUND

Diseases with a genetic basis affect a majority of people during their lifetimes, specifically, syndromic genetic conditions, which, in aggregate, affect nearly 8% of the population and affect health and quality of life. Timely diagnosis allows the clinician to provide optimal health care, by prescribing indicated treatments, initiating screening for associated complications, and instituting supportive therapies where no specific treatment exists. A diagnosis is essential for providing information regarding prognosis and recurrence risk.

However, a proper diagnosis is evasive in many cases because the facial and other physiologic features (phenotypic features) associated with genetic diseases are too subtle to be recognized by a treating physician. Moreover, due to the rarity of many syndromes and the large number of possible disorders, achieving the correct diagnosis may not occur or may involve a lengthy and expensive work-up that may take years or even decades (the diagnostic odyssey). Accordingly, a need exists for systems and methods that address these drawbacks.

SUMMARY

Embodiments consistent with the present disclosure provide systems, methods, and computer-readable media for performing image processing in connection with phenotypic analysis.

Embodiments consistent with the present disclosure provide systems, methods, and computer-readable media for performing image processing in connection with phenotypic analysis. Presently disclosed embodiments may offer one or more advantages over existing methods for diagnosing genetic diseases. For example, some syndromes have recognizable facial and other physiologic features (phenotypic features), which are highly informative but difficult for a physician or clinical geneticist to notice unaided. Recognition of non-classical presentations of common syndromes, or ultra-rare syndromes, may be particularly difficult for medical professional to diagnose unaided. The use of presently disclosed embodiments of computerized systems providing an aid or reference for clinicians, therefore, offers the advantage of making subtle feature differences recognizable at the treatment stage and can also help make a medical expert's knowledge more accessible to healthcare professionals in other specialties, such as pediatrics.

The increased ability provided by presently disclosed embodiments to describe phenotypes in a standardized manner may also enable the identification of new genetic syndromes by matching undiagnosed patients sharing a similar phenotype. Further, presently disclosed matching of geographically dispersed patients with technology may improve the way that genetic syndromes and other genetically caused diseases are studied and explored. Moreover, by combining individual phenotypic findings with individual genomics data, presently disclosed embodiments may enable improved prioritization and interpretation of gene variants, which may lead to rapidly reaching an accurate molecular diagnosis for patients with genetically caused diseases, as well as facilitating research and development of precision medicine solutions.

In one disclosed embodiment, an electronic system for performing image processing in connection with phenotypic analysis may comprise at least one memory for storing computer-executable instructions and at least one processor configured to execute the stored instructions. The at least one processor may execute the instructions to receive electronic numerical information corresponding to pixels reflective of at least one external soft tissue image of an individual and access geographically dispersed genetic information stored in a database. The geographically dispersed genetic information may include numerical data that correlates anomalies in pixels in soft tissue images of a plurality of geographically dispersed individuals to specific genes or to specific genetic variants. The at least one processor may further execute the instructions to compare the electronic numerical information for the individual with the numerical data of the geographically dispersed genetic information stored in a database, to determine at least a likelihood that the individual has at least one pathogenic genetic variant, and prioritize, based on the comparison, one or more genetic variants according to a likelihood of pathogenicity.

In another disclosed embodiment, a computer-implemented method for performing image processing in connection with phenotypic analysis may comprise receiving electronic numerical information corresponding to pixels reflective of at least one external soft tissue image of an individual and accessing geographically dispersed genetic information stored in a database. The geographically dispersed genetic information may include numerical data that correlates anomalies in pixels in soft tissue images of a plurality of geographically dispersed individuals to specific genes or to specific genetic variants. The method may further comprise comparing the electronic numerical information for the individual with the numerical data of the geographically dispersed genetic information stored in a database, to determine at least a likelihood that the individual has at least one pathogenic genetic variant, and prioritizing, based on the comparison, one or more genetic variants according to a likelihood of pathogenicity.

In one disclosed embodiment, an electronic processing system for identifying one or more unknown genetic disorders by analyzing a series of pixels in a plurality of images of external soft tissue may comprise at least one memory for storing computer-executable instructions and at least one processor configured to execute the stored instructions. The at least one processor may execute the stored instructions to identify a first individual with an unknown genetic disorder by analysis of first electronic data reflective of first values corresponding to pixels of an external soft tissue image of the first individual and identify a second individual with another unknown genetic disorder by analysis of second electronic data reflective second values corresponding to second pixels of an external soft tissue image of the second individual. The first values may correspond to relationships between at least one group of pixels in the external soft tissue image of the first individual, and the second values may correspond to relationships between at least one group of pixels in the external soft tissue image of the second individual. The at least one processor may further execute the stored instructions to compare at least some of the analyzed data of the first individual with at least some of the analyzed data of the second individual and determine that the first individual and the second individual are likely to share the unknown genetic disorder.

In another disclosed embodiment, a computer-implemented method identifying one or more unknown genetic disorders by analyzing a series of pixels in a plurality of images of external soft tissue may comprise identifying a first individual with an unknown genetic disorder by analysis of first electronic data reflective of first values corresponding to pixels of an external soft tissue image of the first individual and identifying a second individual with another unknown genetic disorder by analysis of second electronic data reflective second values corresponding to second pixels of an external soft tissue image of the second individual. The first values may correspond to relationships between at least one group of pixels in the external soft tissue image of the first individual, and the second values may correspond to relationships between at least one group of pixels in the external soft tissue image of the second individual. The method may further comprise comparing at least some of the analyzed data of the first individual with at least some of the analyzed data of the second individual and determining that the first individual and the second individual are likely to share the unknown genetic disorder.

In another disclosed embodiment, an electronic processing system for identifying genetic disorders by analyzing a series of pixels in a plurality of images of external soft tissue may comprise at least one memory for storing computer-executable instructions and at least one processor configured to execute the stored instructions. The at least one processor may execute the stored instructions to identify a first individual with an unknown genetic disorder by analysis of first electronic data reflective of first values corresponding to pixels of an external soft tissue image of the first individual and identify a second individual with a known genetic disorder by analysis of second electronic data reflective second values corresponding to second pixels of an external soft tissue image of the second individual. The first values may correspond to relationships between at least one group of pixels in the external soft tissue image of the first individual, and the second values may correspond to relationships between at least one group of pixels in the external soft tissue image of the second individual. The at least one processor may further execute the stored instructions to compare at least some of the analyzed data of the first individual with at least some of the analyzed data of the second individual and determine that the first individual is likely to share the known genetic disorder of the second individual based on the comparison.

In another disclosed embodiment, a computer-implemented method identifying genetic disorders by analyzing a series of pixels in a plurality of images of external soft tissue may comprise identifying a first individual with an unknown genetic disorder by analysis of first electronic data reflective of first values corresponding to pixels of an external soft tissue image of the first individual and identifying a second individual with a known genetic disorder by analysis of second electronic data reflective second values corresponding to second pixels of an external soft tissue image of the second individual. The first values may correspond to relationships between at least one group of pixels in the external soft tissue image of the first individual, and the second values may correspond to relationships between at least one group of pixels in the external soft tissue image of the second individual. The method may further comprise comparing at least some of the analyzed data of the first individual with at least some of the analyzed data of the second individual and determining that the first individual is likely to share the known genetic disorder of the second individual based on the comparison.

The present disclosure also includes non-transitory, computer-readable storage media storing instructions for causing one or more processors to perform any of the methods disclosed herein.

Additional aspects related to the disclosed embodiments will be set forth in part in the description which follows, and in part will be understood from the description, or may be learned by practice of the disclosed embodiments.

It is to be understood that both the foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings.

DETAILED DESCRIPTION

Reference will now be made in detail to the example embodiments, which are illustrated in the accompanying drawings. Wherever possible, the same reference numbers will be used throughout the drawings to refer to the same or like parts.

Embodiments consistent with the present disclosure provide systems, methods, and computer-readable media for performing image processing in connection with phenotypic analysis. Presently disclosed embodiments may offer one or more advantages over existing methods for diagnosing genetic diseases. For example, some syndromes have recognizable facial and other physiologic features (phenotypic features), which are highly informative but difficult for a physician or clinical geneticist to notice unaided. Recognition of non-classical presentations of common syndromes, or ultra-rare syndromes, may be particularly difficult for medical professional to diagnose unaided. The use of presently disclosed embodiments of computerized systems providing an aid or reference for clinicians, therefore, offers the advantage of making subtle feature differences recognizable at the treatment stage and can also help make a medical expert's knowledge more accessible to healthcare professionals in other specialties, such as pediatrics.

The increased ability provided by presently disclosed embodiments to describe phenotypes in a standardized manner may also enable the identification of new genetic syndromes by matching undiagnosed patients sharing a similar phenotype. Further, presently disclosed matching of geographically dispersed patients with technology may improve the way that genetic syndromes and other genetically caused diseases are studied and explored. Moreover, by combining individual phenotypic findings with individual genomics data, presently disclosed embodiments may enable improved prioritization and interpretation of gene variants, which may lead to rapidly reaching an accurate molecular diagnosis for patients with genetically caused diseases, as well as facilitating research and development of precision medicine solutions.

Figure 1:
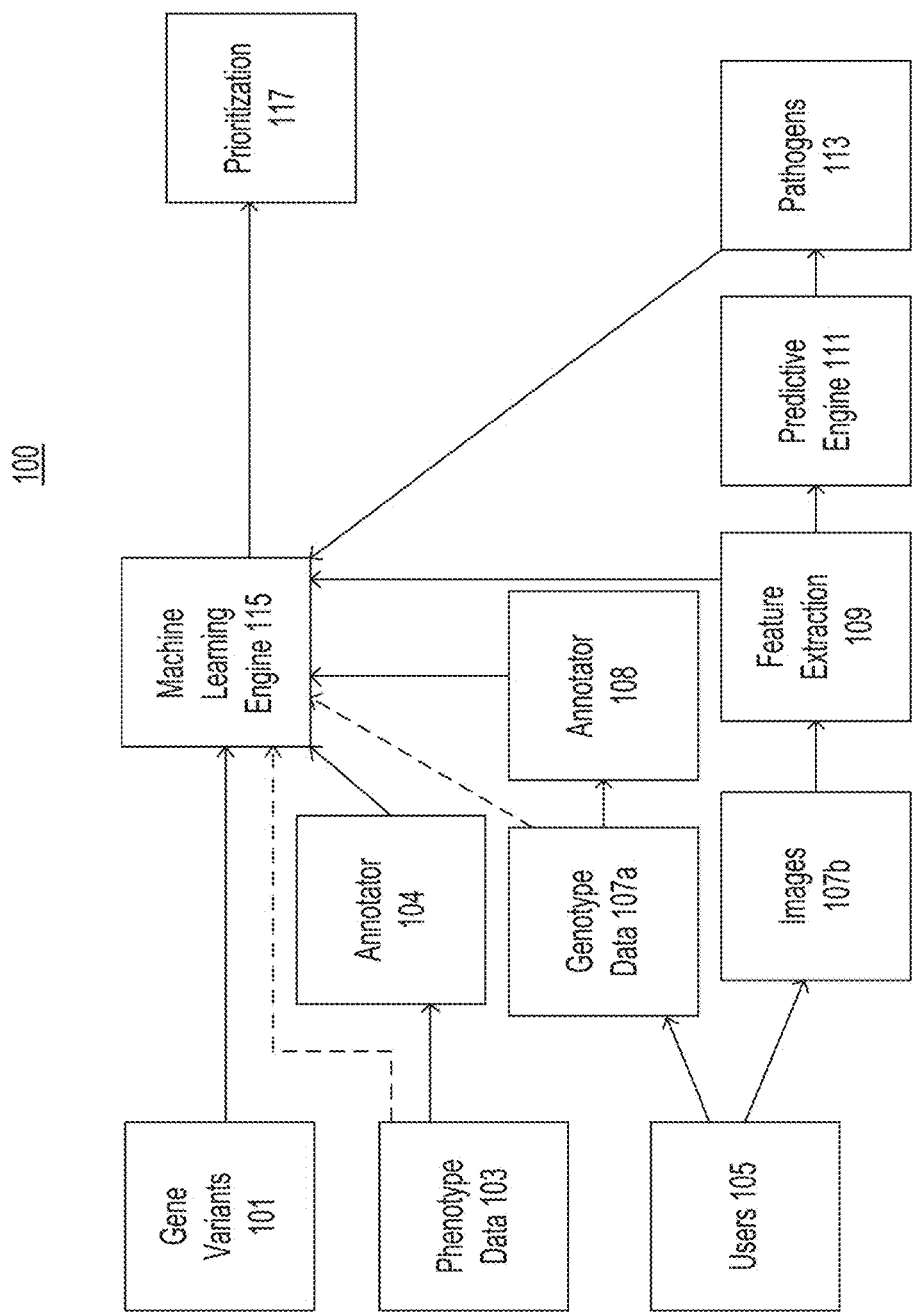
FIG. 1 illustrates an exemplary system for performing image processing in connection with phenotypic and genotypic analysis that may be used for implementing the disclosed embodiments.

FIG. 1 is a diagram illustrating an example system 100 for performing image processing in connection with phenotypic and genotypic analysis, consistent with the disclosed embodiments.

As depicted in FIG. 1, the processing may be performed on information from users 105. As used herein, a "user" may include any individual or organization having information suitable to input into system 100. For example, a "user" may include, among other things, any person or type of person, such as a male or female person and a child or adult. A child may include, for example, a neonate, an infant, a toddler, a preschooler, a school age child, or an adolescent. For example, a male or female person from birth to 1 month old may be referred to as a neonate, from 1 month to 1 year old may be referred to as an infant, from 1 year to 3 years old may be referred to as a toddler, from 3 years to 6 years old may be referred to as a preschooler, from 6 years to 12 years old may be referred to as a school age child, and from 12 years to 18 years old may be referred to as an adolescent. An adult may include, for example, a male or female person from 18 years old and onwards. These age ranges, however, are exemplary only. For example, a 19 year old person may be referred to as an adolescent in certain contexts.

In embodiments described herein, a "user" may comprise a person using an application (e.g., on a mobile phone, tablet, or other device associated with the person) having information (such as phenotype data 103, genotype data 107a, and/or images 107b) that are shared with system 100 (e.g., by consent of the individual when the individual installed the application or otherwise used the application). A "user" may also comprise a genetic testing service or a person using a genetic testing service or other service that shares results (which may, for example, include phenotype data 103, genotype data 107a, and/or images 107b) with system 100 (e.g., by consent of the individual when agreeing to the service). A "user" may also comprise a person whose information (such as phenotype data 103, genotype data 107a, and/or images 107b) was used in one or more research studies that share information with system 100 (e.g., by consent of the individual when agreeing to the study or by virtue of anonymization of the information). Users 105 may therefore comprise any combination of these different kinds of users.

As depicted in FIG. 1, a plurality of inputs may be used by machine learning engine 115. For example, engine 115 may receive gene variants 101. Gene variants 101 may comprise genetic variants that are representations of gene sequences (e.g., stored as text or other format that captures the sequence of cytosine (C), guanine (G), adenine (A) or thymine (T) that form different genes). In some embodiments, gene variants 101 may comprise differential representations. For example, gene variants 101 may comprise a base gene sequence (e.g., stored as text or other format that captures the sequence of C, G, A, and T that forms the base gene) along with differential representations of variants on the base gene observed in a population. The differential representations may comprise a set of locations in the base sequence where a nucleic acid in the variant is different than a corresponding nucleic acid in the base gene linked to an indication of that difference. For example, a differential representation may indicate that location 5 on the base gene has G in the variant gene rather than C like the base gene. In another example, a differential representation may indicate that locations 5 and 6 are null in the variant gene rather than having nucleic acids like the base gene. In yet another example, a differential representation may indicate that the variant gene has extra nucleic acids in a location where the base gene only has one nucleic acid.

In some embodiments, phenotype data 103 may comprise representations of phenotypical characteristics associated with users 105. For example, phenotype data 103 may comprise textual annotations, e.g., by one or more medical professionals, of these characteristics. In such an example, the professional annotations may include words coding for a phenotypic feature, such as "hairy ears," "large forehead," "receding hairline," or the like. Accordingly, the phenotypic features may include descriptions of a medical professional observation of an anatomical feature. Phenotype data 103 may therefore be retrieved from one or more medical records associated with users 105 (e.g., obtained via consent of users 105 and/or anonymized to avoid traceability to users 105).

In some embodiments, as depicted with the dashed line of FIG. 1, phenotype data 103 may be directly input into machine learning engine 115. Additionally or alternatively, as depicted with the solid line of FIG. 1, phenotype data 103 may be input to annotator 104, which encodes annotations that are then input into machine learning engine 115. For example, annotator 104 may encode using machine learning such as a neural network that outputs a pathogenic score associated with the annotations, one or more feature vectors associated with the annotations, or the like. Alternatively, annotator 104 may convert descriptors of phenotypical characteristics to numerical representations of such characteristics. For example, a vector of various dimensions (such as "short neck," "narrow eyes," or the like) may be populated based on phrases or other content of the representations.

Additionally or alternatively, phenotype data 103 may be received from users 105. For example, users 105 may use an application (e.g., on a mobile phone, tablet, or other device associated with the person) into which users 105 enter phenotype data 103 that are shared with system 100 (e.g., by consent of the individual when the individual installed the application or otherwise used the application). In such an example, phenotype data 103 may comprise textual descriptions input or otherwise selected by users 105. Additionally or alternatively, phenotype data 103 may comprise graphic data. For example, users 105 may use an application (e.g., on a mobile phone, tablet, or other device associated with the person) into which users 105 provide images (e.g., of a face or other external soft tissue) comprising phenotype data 103 that are shared with system 100 (e.g., by consent of the individual when the individual installed the application or otherwise used the application). In such embodiments, the images may be de-identifying, e.g., by using one or more neural networks before transmission to system 100 and/or at system 100.

In some embodiments, genotype data 107a may comprise representations of one or more genes of users 105. For example, genotype data 107a may comprise sequences of the one or more genes. Accordingly, genotype data 107a may be textual. Moreover, as depicted with the dashed lines of FIG. 1, may be input directly into machine learning engine 115. Additionally or alternatively, as depicted with the solid lines of FIG. 1, genotype data 107a may be to annotator 108, which encodes annotations that are then input into machine learning engine 115. For example, annotator 108 may output annotations indicating one or more genes of interest, such as gene variants 101. In such an example, annotator 108 may convert genotype data 107a to numerical representations, such as vectors, encoding the presence of one or more genes of interests, such as gene variants 101. Additionally or alternatively, annotator 108 may output an encoded genome, e.g., encoded using machine learning such as a neural network that outputs a pathogenic score associated with the genome, one or more feature vectors associated with the genome, or the like.

Although depicted as associated with users 105 in FIG. 1, genotype data 107a may be anonymized, e.g., through the use of random identifiers, non-traceable identifiers, or the like. Genotype data 107a may be received from users 105 (e.g., using an application as described above), received from a genetic testing service that users 105 ordered and/or subscribe to, received from genetic testing used by medical professionals and/or researchers that treated and/or studied users 105, or the like. In embodiments where genotype data 107a are received from a testing service or from medical professionals and/or researchers, genotype data 107a may include the annotations comprising phenotype data 105, as described above.

Genotype data 107a may be provided in any suitable data format, which may include a complete set of genetic data for an individual or a partial set of data that provides an individual's variations from a reference genome. For example, genotype data 107a may be provided in a general feature format (GFF) storing an individual's complete genetic data. For further example, genotype data 107a may be provided in a variant call format (VCF) in which an individual's variations are stored in reference to a reference genome. Indeed, any suitable text file storing genetic information may be used as the genotype data 107a.

In some embodiments, images 107b may comprise visual representations of one or more of users 105 (or portions thereof, such as faces or other external soft tissues). As depicted in FIG. 1, images 107b may undergo feature extraction 109. As used in the context of images, the term "feature" refers to any property of images 107b (such as points, edges, gradients, or the like) or to any property of a face or other tissue representable by an image (such as a phenotypic feature). More broadly, "feature" may refer to any numerical representation of characteristics of a set of data, such as characteristics of text (e.g., based on words or phrases of the text), characteristics of genes (e.g., the presence one or more gene variants, locations of particular genes), characteristics of images (as explained above), or the like. A "feature" may be numerically represented with scalars or with vectors. For example, feature extraction 109 may include application of one or more layers of one or more neural networks, such as convolutional layers, deconvolutional layers, fully connected layers, other activation layers, and the like; one or more max pooling steps; one or more average pooling steps; or any combination thereof (as described below with respect to FIG. 2). Features extracted using feature extraction 109 (such as one or more vectors from pooling steps of feature extraction 109) may be input to system 100 rather than images 107b themselves. Accordingly, the input may be de-identified from users 105.

As further depicted in FIG. 1, feature extraction 109 may output features (e.g., vectors) to predictive engine 111. Predictive engine 111 may comprise a machine learned model that accepts one or more features from one or more external soft tissue images as input and outputs one or more possible pathogens (pathogens 113) based on the one or more features. For example, predictive engine 111 may comprise a decision tree, a neural network, or other machine learning algorithm trained using one or more annotated data sets. Accordingly, predictive engine 111 may have been trained using feature vectors annotated with pathogens, e.g., from one or more professionals. In embodiments where predictive engine 111 comprises one or more neural networks, weights and activation functions of nodes of the network(s) may have adjusted such that the outputs converge toward the annotations. Training may end after a certain level of accuracy has been reached.

In some embodiments, predictive engine 111 may output confidence scores or may rank (e.g., by confidence scores) the one or more possible pathogens. Accordingly, machine learning engine 115 may filter the pathogens output from predictive engine 111, e.g., by imposing a confidence score threshold and/or a ranking cutoff.

Machine learning engine 115 may therefore accept one or more of gene variants 101, phenotype data 103, genotype data 107a, features from feature extraction 109, and/or pathogens 113 from predictive engine 111 as input. Machine learning engine 115 may output a prioritized list of one or more genes or genetic variants according to a pathogenicity (prioritization 117) for a given individual. Indeed, although the methods described herein are described as prioritizing genetic variants, it should be understood that in some embodiments, genes, genetic variants, or both may be prioritized.

During a training phase, annotations of known gene variants associated with known pathogens may be used for training. For example, based on gene variants 101, phenotype data 103, genotype data 107a, features from feature extraction 109, and/or pathogens 113 from predictive engine 111 as input, machine learning engine 115 may output one or more genetic variants associated with pathogens. As explained above, for each pathogen, one or more possible variants may be prioritized by pathogenicity (or likelihood of being linked to the pathogen). Accordingly, machine learning engine 115 looks for correlations between the features across one or more portions of users 105 that match correlations between pathogens 113 and gene variants 101 present in genotype data 107a across the one or more portions of users 105. In embodiments where machine learning engine 115 comprises one or more neural networks, machine leaning engine 115 may then have weights or activation functions for nodes therein adjusted such that the outputted prioritized variants converge on the known gene variants and that the outputted pathogens associated with the prioritized variants converge on the known pathogens.

During a testing or refinement phase, users 105 may comprise one or more new persons. In this phase, genotype data 107a and/or pathogens 113 may be used as annotations. Using the new persons, machine learning engine 115 may operate on gene variants 101, phenotype data 103, features from feature extraction 109, and/or one of genotype data 107a and pathogens 113 from predictive engine 111 to output possible genetic variants and/or possible pathogens expected in users 105. Machine learning model 119 may be refined, e.g., by adjusting weights or activation functions of nodes thereof in embodiments where machine learning model 119 comprises a neural network, to converge the outputted variants to gene variants 101 present in genotype data 107a and/or to converge the outputted pathogens to pathogens 113 predicted by predictive engine 111. As explained above, converging may continue until a threshold level of accuracy is obtained.

During a use phase, users 105 may include an individual not previously in a training and/or testing set, as explained above. In this phase, the individual may lack genotype data 107a and therefore lack annotations. Using the individual, machine learning engine 115 may operate on gene variants 101, phenotype data 103, features from feature extraction 109, and/or pathogens 113 from predictive engine 111 to output and rank possible genetic variants expected in users 105.

Figure 2:
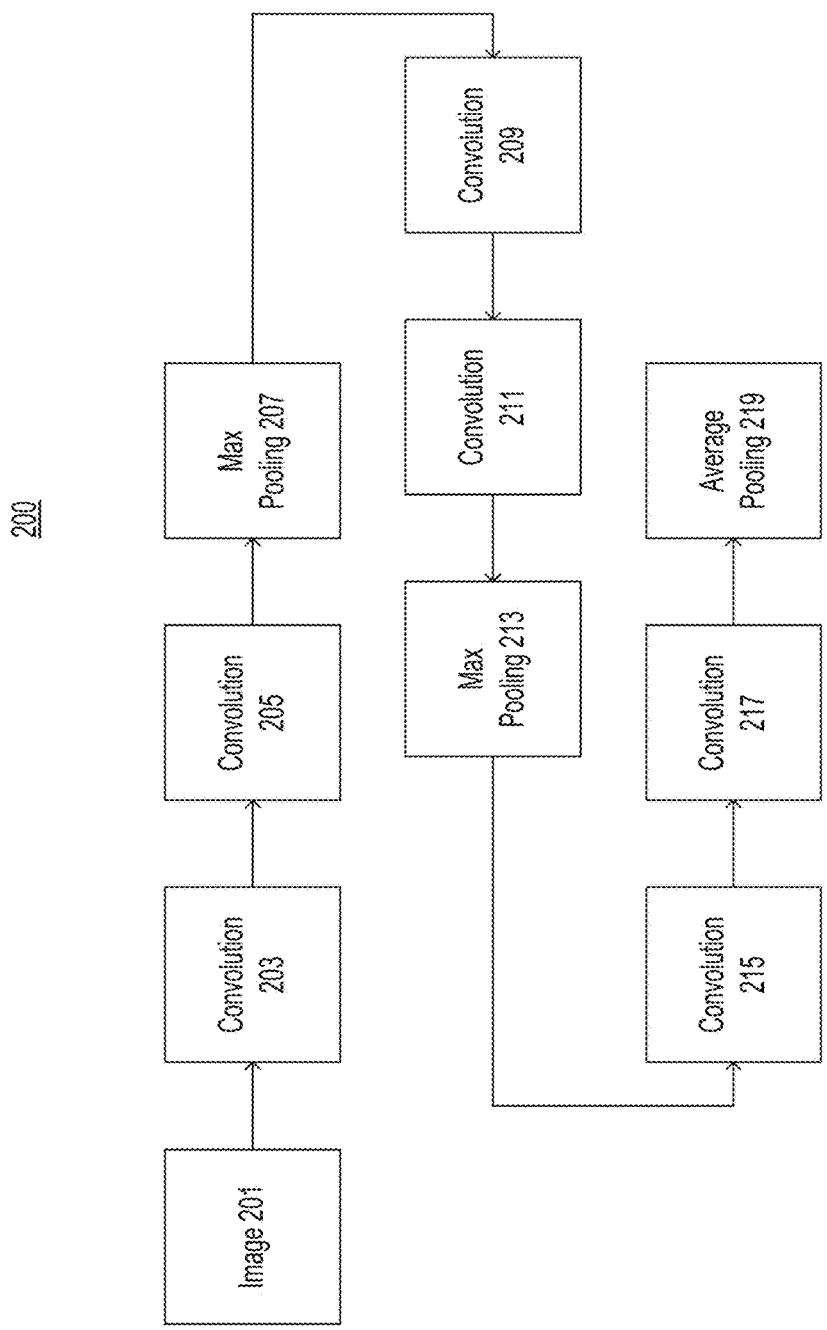
FIG. 2 illustrates an exemplary pipeline for de-identifying images of external soft tissue.

FIG. 2 illustrates an exemplary pipeline 200 that one or more processors (e.g., processor 410 of device 400 of FIG. 4) may be configured to implement. For example, as discussed below, processor 410 may be configured to implement pipeline 200 by executing software or firmware stored in memory device 420, or may be configured to implement pipeline 200 using dedicated hardware or one or more ASICs.

As depicted in FIG. 2, an image 101 may be de-identified. For example, image 101 may be input to one or more convolutional layers, e.g., layers 203 and 205, whose outputs are then pooled using max pooling 207. One of more additional convolutional layers coupled with one or more pooling steps may be implemented, such as convolutional layers 209 and 211, whose outputs are then pooled using max pooling 213, convolutional layers 215 and 217, whose outputs are then pooled using average pooling 219, or the like. In some embodiments, average pooling or any other function that combines any amount of the layers in the network into a single descriptor vector may comprise the feature used by machine learning engine 115. In other embodiments, one or more normalization functions, such as a softmax function, may normalize the length of all feature vectors output by the average pooling, e.g., by normalizing the vectors such that they sum to 1. Additionally or alternative, a fully connected layer (e.g., with dropout 0.5) may operate on average pooling such that the output of the fully connected layer (which may be normalized afterward) is the feature used by machine learning engine 115.

Although not depicted, pipeline 200 may further include a rectified linear unit and/or batch normalization after one or more pooling steps. For example, the rectified linear unit and/or batch normalization may be included after max pooling 207 and max pooling 213 but not after average pooling 219. De-identification may therefore be achieved using at least one of the reduced resolution provided by the pooling steps, nonlinearity (and thus difficult reversibility) of the rectified linear unit, and transformation (and thus difficult reversibility) of the batch normalization. A combination of such techniques provides a technical advantage by ensuring anonymity of the features to avoid inadvertently exposing image 101, which may comprise personal health information (PHI), in ways that do not comply with privacy laws and regulations. Moreover, the anonymity is achieved automatically using rules (that is, using pipeline 200) rather than using manual, subject techniques to do so.

Although depicted using three sets of steps with two convolutional layers per steps, other structures may be included as pipeline 200, such as four series of steps, five series of steps, or the like. Although depicted with a structure of two convolutional layers followed by pooling, other structures may be used as pipeline 200, such as three convolutional layers followed by pooling, a varying number of convolutional layers followed by pooling, or the like.

Figure 3:
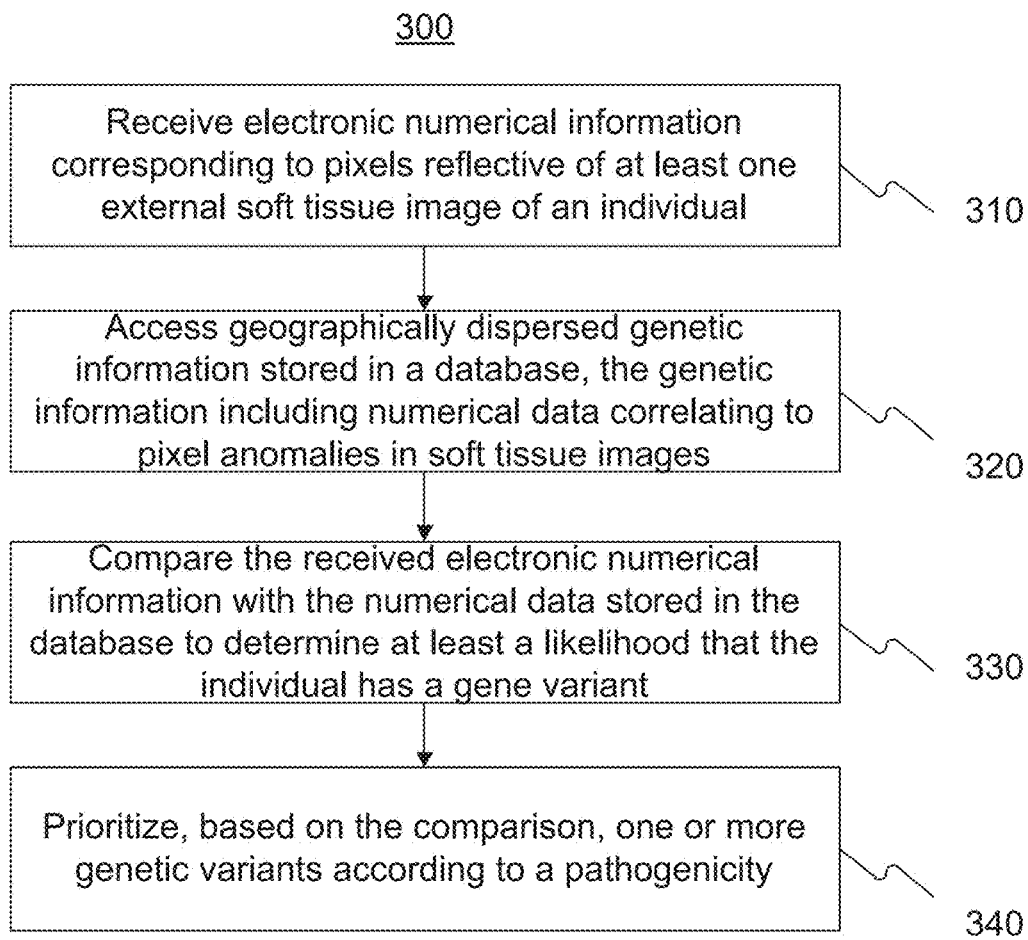
FIG. 3 illustrates example operations that a processor may be configured to perform to process images in connection with phenotypic and genotypic analysis, in accordance with some of the disclosed embodiments.

FIG. 3 illustrates an exemplary process 300 that one or more processors (e.g., processor 410 of device 400 of FIG. 4) may be configured to perform. For example, as example, as discussed below, processor 410 may be configured to perform process 300 by executing software or firmware stored in memory device 420, or may be configured to perform process 300 using dedicated hardware or one or more application-specific integrated circuits (ASICs).

Processor 410 may be configured to receive electronic numerical information corresponding to pixels reflective of at least one external soft tissue image of an individual (step 310). For example, as described above, processor 410 may be received from an application on, for example, a mobile phone, tablet, or other device associated with the individual. In some embodiments, the at least one external soft tissue image of the individual may be two-dimensional.

In some embodiments, the electronic numerical information may comprise de-identified representations of the at least one external soft tissue image. For example, as explained above, the electronic numerical information may be one or more feature vectors extracted from one or more pooling steps of a neural network. In such embodiments, the de-identification may have been performed using one or more convolutional neural networks, which may include one or more convolutional layers and one or more pooling steps. For example, the electronic numerical information may comprise the output of average pooling 219 (or of a fully connected layer and/or a softmax function implemented after average pooling 219) of pipeline 200 of FIG. 2, described above.

Processor 410 may be configured to access geographically dispersed genetic information stored in a database (step 320). The geographically dispersed genetic information may include numerical data that correlates anomalies in pixels in soft tissue images of a plurality of geographically dispersed individuals to specific genes or to specific genetic variants. For example, processor 410 may access a relational database including gene sequence and/or identifications of particular genes (e.g., by storing indicators of locations of the particular genes in chromosomes) mapped to anomalies in pixels (e.g., stored as feature vectors). As used herein, "geographically dispersed" refers to information that is associated with a particular measure of geographic variety, such as a minimum median distance between the plurality of geographically dispersed individuals, a maximum local density of the plurality of geographically dispersed individuals, or the like.

In some embodiments, the geographically dispersed genetic information may include genetic test information. For example, the plurality of geographically dispersed individuals may have participated in a research study or in a commercial test such as AncestryDNA®, 23andMe, or the like. In such embodiments, the genetic test information may be annotated. For example, as explained above, the genetic test information may include one or more medical professional annotations. In some embodiments, the annotations may include words coding for a phenotypic feature. For example, as explained above, the phenotypic features may include description of a medical professional observation of an anatomical feature.

Processor 410 may be configured to compare the electronic numerical information for the individual with the numerical data of the geographically dispersed genetic information stored in a database (step 330). Processor 410 may use the comparison to determine at least a likelihood that the individual has a specific genetic variant. For example, as explained above with respect to FIG. 1, processor 410 may use one or more trained models to determine the likelihood. Processor 410 may thus use machine learning engine 115 of FIG. 1, described above to determine the likelihood.

In some embodiments, processor 410 may also use pathogen information derived from the electronic numerical information to determine the likelihood. For example, as explained above with respect to FIG. 1, machine learning engine 115 may receive pathogens 113 predicted using a predictive engine 111 applied to the electronic numerical information (that is, features extracted using feature extraction 109).

Processor 410 may further be configured to prioritize, based on the comparison, one or more genetic variants according to a pathogenicity (step 340). For example, during a training phase, processor 410 may perform the prioritization to compare to known genes and known pathogens in order to converge associations between the inputs to processor 410 and the output priority. In another example, during an operation phase, processor 410 may perform the prioritization to output to researchers for use in determining gene variants of interest.

In some embodiments, prioritizing may include assigning the one or more genetic variants to at least one pathogenicity class. For example, gene variants may be associated with one or more pathogens (or associated with at least one class of pathogens) before ranking by likelihood of association. Accordingly, the prioritization may be by pathogen (or by class) rather than overall.

Method 300 may include further steps. For example, processor 410 may be further configured to access phenotypic data associated with the individual and/or phenotypic data associated with the plurality of geographically dispersed individuals. As explained above, the phenotypic data may be textual.

In such embodiments, as explained above, the phenotypic data associated with the individual may have been received from the individual and/or the phenotypic data associated with the plurality of geographically dispersed individuals may have been received from the individuals. Moreover, in such embodiments, the prioritizing may be further based on a comparison of the textual phenotypic data of the individual with the phenotypic data of the geographically dispersed individuals. For example, as explained above, correlations between phenotypic data of the individual and the phenotypic data of the geographically dispersed individuals may be used with correlations between the electronic numerical information for the individual and the numerical data of the geographically dispersed genetic information stored in a database to identify likely genetic variants of the individual (as explained in step 330) and/or to prioritize gene variants (as explained in step 340).

Additionally or alternatively, method 300 may include de-identifying the at least one external soft tissue image using one or more convolutional neural networks. For example, as explained above with respect to pipeline 200 of FIG. 2, processor 410 may apply one or more convolutional layers and/or one or more pooling steps to de-identify the at least one external soft tissue image. Accordingly, de-identification of the image may result in electronic numerical information corresponding to pixels of the image comprising feature vectors output by the one or more pooling steps (or by a fully connected layer and/or a softmax function implemented after one or more pooling steps).

Figure 4:
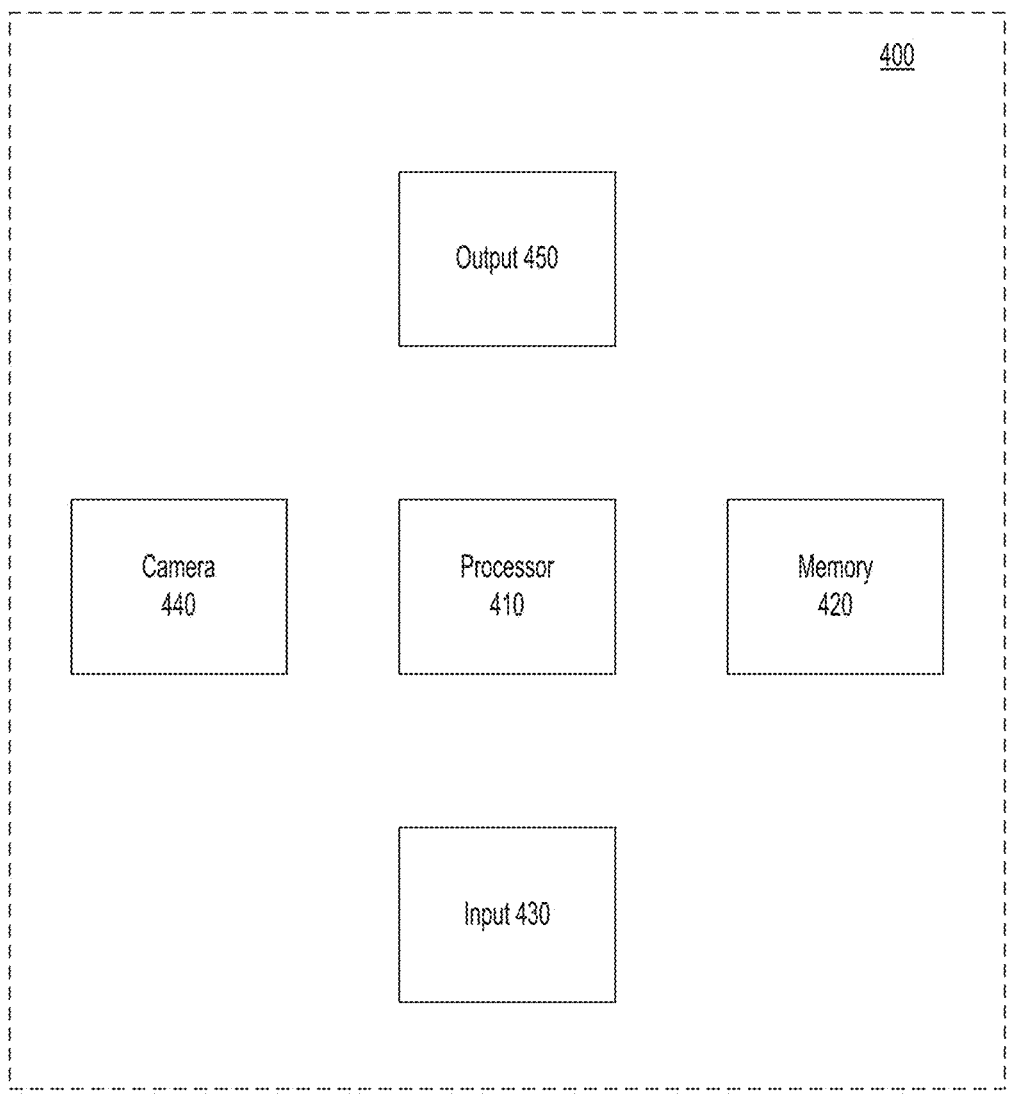
FIG. 4 illustrates an example system for performing image processing in connection with phenotypic and genotypic analysis that may be used for implementing the disclosed embodiments.

FIG. 4 illustrates an exemplary device 400 for implementing the above systems and methods (such as method 300 of FIG. 3). Device 400 may include, among other things, at least one processor 410, at least one memory device 420, at least one input device 430, at least one camera 440, and at least one output device 450.

Processor 410 may include any electrical circuit that may be configured to perform an operation on at least one input variable, including, for example one or more integrated circuits, microchips, microcontrollers, and microprocessors, which may be all or part of a central processing unit (CPU), a digital signal processor (DSP), a field programmable gate array (FPGA), a graphical processing unit (GPU), or any other circuit known to those skilled in the art that may be suitable for executing instructions or performing logic operations. Multiple functions may be accomplished using a single processor or multiple related and/or unrelated functions may be divided among multiple processors.

Processor 410 may be configured to access memory device 420, which may include, for example, persistent memory, ROM, EEPROM, EAROM, flash memory devices, magnetic disks, magneto optical disks, CD-ROM, DVD-ROM, Blu-ray, and the like. Memory device 120 may contain instructions (i.e., software or firmware) or other data. Processor 410 may receive instructions and data stored memory device 420. Thus, in some embodiments, processor 110 may execute the software or firmware to perform functions by operating on input data and generating output. For example, the functions may comprise method 300 of FIG. 3, described above.

Additionally or alternatively, processor 410 may also receive or access data stored remotely over a network (not depicted in FIG. 4). For example, device 400 may include a communication device, such as a network interface controller, (not depicted in FIG. 4) that enables processor 410 to receive or access data stored remotely on a server or user device over a network.

In some embodiments, processor 410 may be, for example, dedicated hardware or an ASIC that performs processes by operating on input data and generating output. For example, the functions may comprise method 300 of FIG. 3, described above. Processor 410 may be any combination of dedicated hardware, one or more ASICs, one or more general purpose processors, one or more DSPs, one or more GPUs, or one or more other processors capable of processing digital information. For example, as explained above, processor 410 may comprise multiple processors that may provide parallel processing capabilities.

Figure 5A:
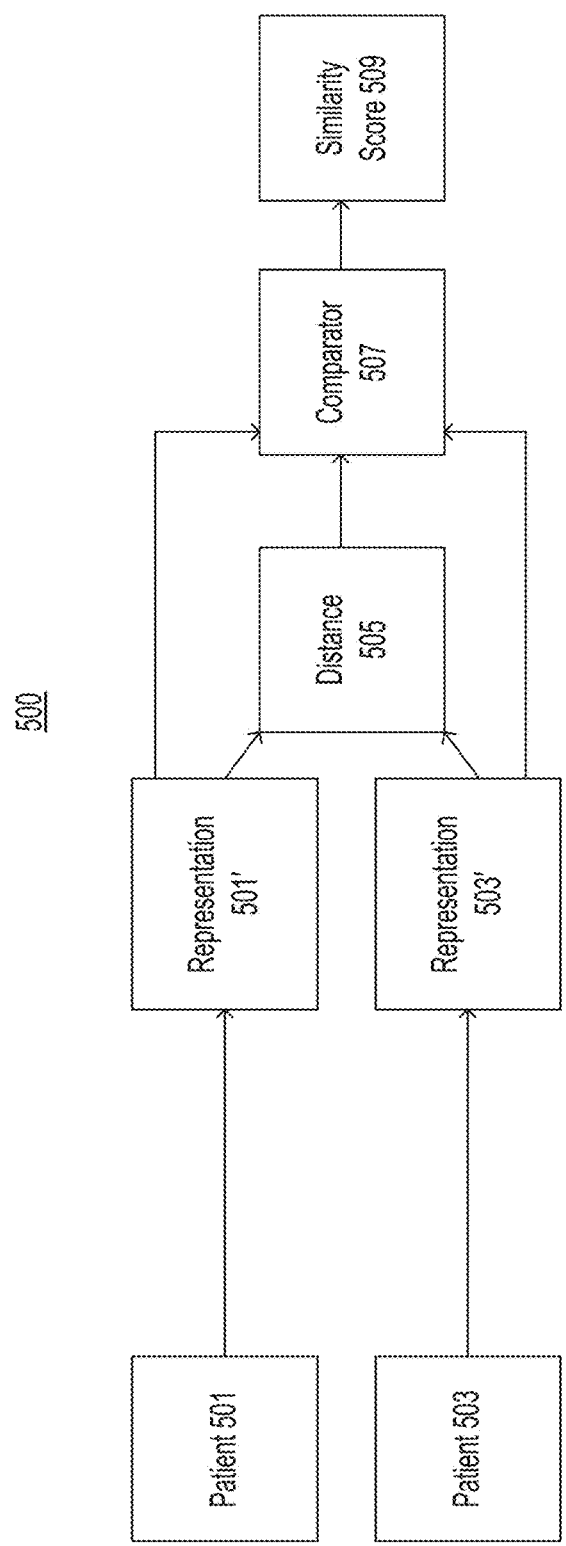
FIG. 5A illustrates an exemplary system for patient matching using phenotypic analysis that may be used for implementing the disclosed embodiments.

FIG. 5A is a diagram illustrating an example system 500 for patient matching using phenotypic analysis, consistent with the disclosed embodiments. As depicted in FIG. 5A, the patient matching may be performed for a first patient 501 and a second patient 503. As used herein, a "patient" may include any individual having information input into system 500. For example, a "patient" may include, among other things, any person or type of person, such as a male or female person and a child or adult. A child may include, for example, a neonate, an infant, a toddler, a preschooler, a school age child, or an adolescent. For example, a male or female person from birth to 1 month old may be referred to as a neonate, from 1 month to 1 year old may be referred to as an infant, from 1 year to 3 years old may be referred to as a toddler, from 3 years to 6 years old may be referred to as a preschooler, from 6 years to 12 years old may be referred to as a school age child, and from 12 years to 18 years old may be referred to as an adolescent. An adult may include, for example, a male or female person from 18 years old and onwards. These age ranges, however, are exemplary only. For example, a 19 year old person may be referred to as an adolescent in certain contexts.

As depicted in FIG. 5A, the patient matching may be performed using image analysis. For example, patient 501 may be associated with one or more representations of patient 501, such as representation 501'. The representations 501' may be any type of data representative of the patient's phenotype. For example, the representations 501' may be of external soft tissue (such as a face or other external soft tissue). For example, representation 501' may comprise a digital representation of the external soft tissue, such as an image. Additionally or alternatively, representation 501' may comprise electronic data reflective of first values corresponding to pixels of the digital representation. For example, as explained below with respect to FIG. 6, the electronic data may comprise one or more features (e.g., represented as one or more vectors) extracted by one or more neural networks. Similarly, patient 503 may be associated with one or more representations 503' of the phenotype of the patient 503. For example, the representation 503' may represent the external soft tissue (such as a face or other external soft tissue) of patient 503.

The representations 501' and 503' may include any type of data representing the phenotype of the respective patient. For example, representations may include camera images, medical images (e.g., ultrasonic images, magnetic resonance images (MRI), positron emission tomography (PET) images, X-ray images, etc.), annotated textual information (e.g., a doctor's notes, a patient's documentation of symptoms or features), or any other data representative of the patient's phenotype. Accordingly, representation 501' may additionally or alternatively include or otherwise be based on other known information regarding patient 501, such as text related to the user (e.g., describing one or more diagnoses of patient 501, describing one or more doctor visits of or medical procedures performed on patient 501, describing one or more phenotypic features of patient 501, or the like), medical images of the patient 501 (e.g., a magnetic resonance imaging (MRI) image or the like), genotype data associated with the patient 501 (e.g., sequences of the genome of patient 501, indicators of whether patient 501 has one or more gene variants, or the like), etc. Representation 501' may thus comprise a numerical representation, such as a vector, based on the information regarding patient 501 included in representation 501'.

As further depicted in FIG. 5A, system 500 may determine a distance 505 between representations 501' and 503'. For example, in embodiments where representations 501' and 503' comprise electronic data reflective of first values corresponding to pixels of the digital representation, distance 505 may comprise a matrix of differential values of the electronic data. Accordingly, in embodiments where representations 501' and 503' comprise feature vectors extracted using neural networks (e.g., pipeline 200 of FIG. 2 and/or pipeline 600 of FIG. 6), distance 505 may comprise one or more difference vectors between the one or more vectors comprising representation 501' and the one or more vectors comprising representation 503'. In some embodiments, distance 505 may comprise the length of such difference vectors rather than the vectors themselves.

Additionally or alternatively, distance 505 may comprise differences in pixel intensity in corresponding regions of the electronic data for each of the first and second individual. For example, representations 501' and 503' may comprise images or pixel data output from one or more layers of one or more neural networks, such as convolutional layers, deconvolutional layers, fully connected layers, other activation layers, and the like. Accordingly, pixel intensity may be compared.

System 500 may use a comparator 507 to compare representations 501' and 503'. In some embodiments, as depicted in FIG. 5A, distance 505 may be used as well. In other embodiments, system 500 may compare representations 501' and 503' without determining distance 505.

Comparator 507 may output a similarity score 509 (e.g., a real value or a vector) indicating the similarity between representations 501' and 503'. In embodiments where the score comprises a vector or other collection of values, the scores may be localized to various portions of representations 501' and 503'. For example, the output may indicate that a region of interest, such as the nose, in representations 501' and 503' is similar but that a different region of interest, such as the ears, in not. As used herein, the term "similar" may refer not only to pixel-based similarity (e.g., in color, shape, size, or the like) but also to feature-based similarity (e.g., resulting in similar feature vectors being output from one or more neural networks).

Comparator 507 may comprise a machine learned model that accepts representations 501' and 503' (and optionally distance 505) as input and outputs the similarity score 509 based on representations 501' and 503'. For example, comparator 507 may comprise a decision tree, a neural network, or other machine learning algorithm trained using one or more annotated data sets. Accordingly, comparator 507 may have been trained using representations annotated with similarity scores, e.g., from one or more professionals. In embodiments where comparator 507 comprises one or more neural networks, weights and activation functions of nodes of the network(s) may have adjusted such that the outputs converge toward the annotations. Training may end after a certain level of accuracy has been reached. Alternatively, comparator 507 may comprise one or more predefined (rather than trained) functions that calculate a similarity score between representations.

Figure 5B:
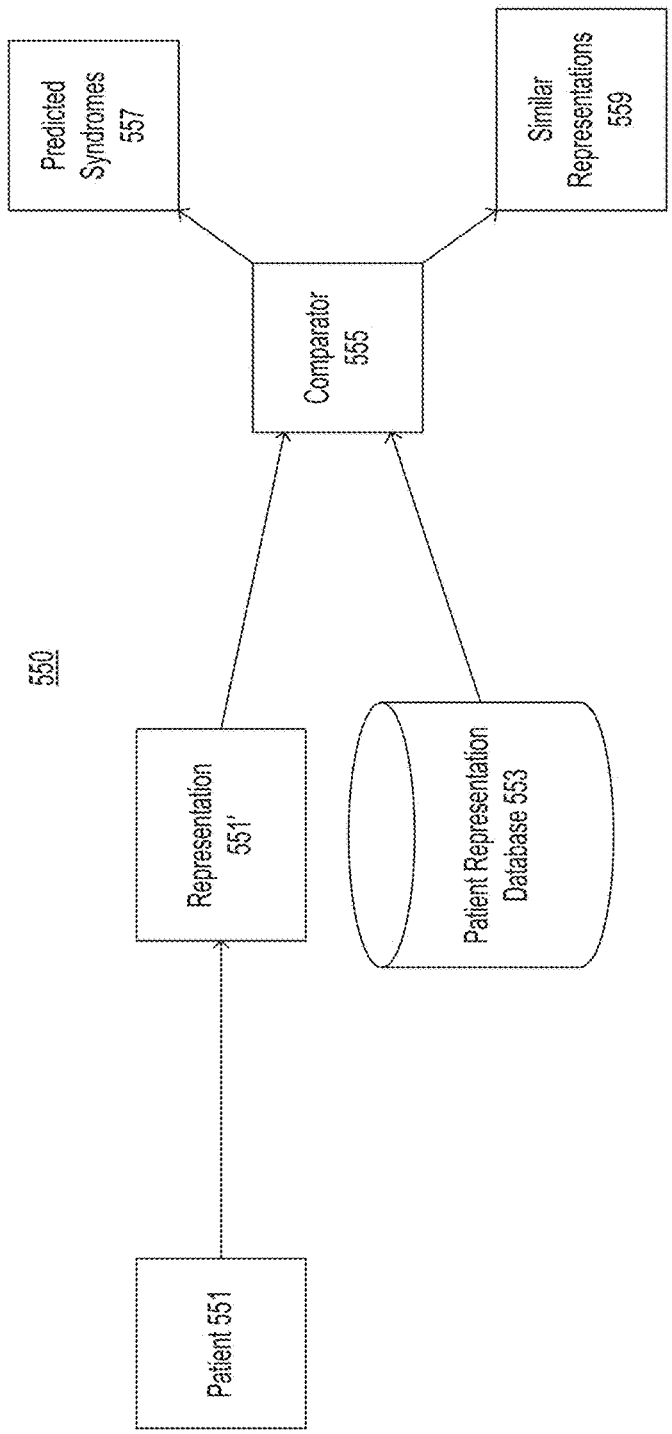
FIG. 5B illustrates an exemplary system for using patient matching to predict shared syndromes that may be used for implementing the disclosed embodiments.

FIG. 5B is a diagram illustrating an example system 550 for using patient matching to predict shared syndromes, consistent with the disclosed embodiments. As depicted in FIG. 5B, the patient matching may be performed using image analysis. For example, patient 551 may be associated with one or more representations of external soft tissue (such as a face or other external soft tissue) of patient 551, such as representation 551'. For example, representation 551' may comprise a digital representation of the external soft tissue, such as an image, and/or electronic data reflective of first values corresponding to pixels of the digital representation, similar to representation 501' of FIG. 5A.

As further depicted in FIG. 5B, system 550 may include or access a patient representation database 553. Database 553 may store information associated with a plurality of patients. Database 553 may be indexed by patient or by anonymous identifiers of patients, e.g., random identifiers, non-traceable identifiers, or the like. One or more representations of external soft tissue, similar to representation 551' may be stored for each patient in database 553.

Database 553 may also store symptoms reported by patients, e.g., as extracted from or included in medical records associated with the patients. Treatments undergone for such symptoms may also be stored in database 553. In some embodiments, database 553 may also be indexed by the stored symptoms and/or the stored treatments.

In some embodiments, database 553 may also store genetic data associated with the patients. For example, the genetic data a complete set of genetic data for patients or a partial set of data that provides patients' variations from a reference genome. For example, the genetic data may be provided in a general feature format (GFF) storing patients' complete genetic data. For further example, the genetic data may be provided in a variant call format (VCF) in which patients' variations are stored in reference to a reference genome. Indeed, any suitable text file storing genetic information may be used as the genetic data. Additionally or alternatively, the genetic may comprise an annotated genome, e.g., with annotations indicating one or more genes of interest, such as gene variants. Additionally or alternatively, the genetic may comprise an encoded genome, e.g., encoded using machine learning such as a neural network that outputs a pathogenic score associated with the genome, one or more feature vectors associated with the genome, or the like.

Comparator 555 may therefore accept any available information from database 553 as input, such as representations of external soft tissue, genetic data, symptoms, and/or treatments. Although not depicted in FIG. 5B, genetic data, symptoms, treatments, and other data used from database 553 as input may also be input for patient 551.

Similar to comparator 507 of FIG. 5A, comparator 555 may output similarity scores indicating the similarity between representations in database 553 and a representation of patient 551. Accordingly, as depicted in FIG. 5B, comparator 555 may be used to form a list 559 of similar representations stored in database 553. For example, comparator 555 may operate on a plurality of representations stored in database and then use one or more thresholds on the similarity score(s) for each representation to determine whether to include each representation on list 559. The thresholds may be predetermined, selected by a professional using comparator 555, or developed using a machine learning model subject to constraints of accuracy and inclusion.

Additionally or alternatively, comparator 555 may output a list 557 of predicted syndromes that may be shared by patients in database 553 and patient 551. For example, the patients in database 553 sharing the syndromes with patient 551 may comprise patients having representations on list 559. The syndromes may be extracted from database 553 for the patients included on list 559. Accordingly, any syndromes associated with at least a threshold number (or percentage) of patients included on list 559 may be output on list 557. Alternatively, list 557 may comprise a list of symptoms that may be shared by patients in database 553 and patient 551. Accordingly, any symptoms shared by patients having similar representations may be output. Such output may be indicative of a shared genetic disease that may not be yet recognized (and therefore not stored) as a syndrome in database 553.

In some embodiments, the features of systems 500 and 550 may be used in combination to match two or more patients who are likely to share the same (or a similar) medical condition. For example, in one embodiment, a first physician may be treating patient 501 while a second physician is treating patient 503. The patients 501 and 503 may share a common phenotype that is not discernible to the physician's eye but is inherent in some or all of the patient's data. The data from each of patients 501 and 503 may be compared to the learned data in database 553 to match the patients 501 and 503 based on phenotypic similarities that are discernible by the machine learning engine but may not be observable or readily observable by the physician. Based on a phenotypic similarity score, the system may identify the patients 501 and 503 as being matched with respect to a shared unknown medical condition.

Although described above as matching patient 501 with patient 503 or as matching patient 551 to one or more patients in database 553, systems 500 and 550 may also accept a plurality of patients as input (e.g., from database 553 or externally input) and then match the plurality of patients amongst each other. For example, systems 500 and 550 may classify the patients according to distances, similarities (e.g., similarity scores), matches (e.g., complementary matches identified as described above), or the like.

In some embodiments, the first patient 501 may show symptoms that indicate that he has a first unknown medical condition (e.g., disease). Likewise, the second patient 503 may show symptoms that indicate that he has a second unknown medical condition (e.g., disease). However, in other embodiments, the patients may not be showing any symptoms of having a medical condition (e.g., medical data may be collected at routine visits to the doctor) when they are matched. For example, in one embodiment, patient 501 may have a known medical condition for which a phenotypic feature is indicative. The patient 503 may be found to have a high similarity score for the same phenotypic feature. Thus, the patient 503 may be matched with patient 501, thus increasing the likelihood that the patient 503 may receive a diagnosis before becoming symptomatic.

As used herein, an unknown medical condition may be a condition that is not known to one or more individuals at a given point in time. For example, in one embodiment, an unknown medical condition may be one that the patient, the patient's medical provider, or both do not know that the patient has. In another embodiment, an unknown medical condition may be a condition that has not yet been recognized by the medical community. For example, an unknown medical condition may be one that does not have a recognizable name in the medical community. For further example, an unknown medical condition may be one that has not yet been defined by the medical community according to symptoms, causes, and/or treatments. The unknown medical condition may be unknown at a given point in time, such as at the time when the patients are matched.

In some embodiments, medical professionals may be matched based on the matching of the patients described above. For example, medical professionals may be matched if a first medical professional is treating a first patient with an undiagnosed condition and a second medical professional is treating a second patient with a diagnosed condition if the first and second patient are assigned a high enough similarity score to be matched. In this way, the machine learning engine may increase the likelihood that the first medical professional is able to correctly diagnose and treat the first patient.

In another embodiment, both the first and second patient may be symptomatic but undiagnosed. If the machine learning engine matches the two patients, the first and second medical professionals may be matched to enable collaboration and identification of additional patients who may have a rare or unknown disease. Additionally or alternatively, genomic information associated with the matched patients may be provided to one or more medical professionals as likely candidates for the rare or unknown diseases. Accordingly, in some embodiments researchers may use the genomic information to assess the possibility of a new genetic disease, without the matched patients being identified, thus preserving privacy.

Figure 6:
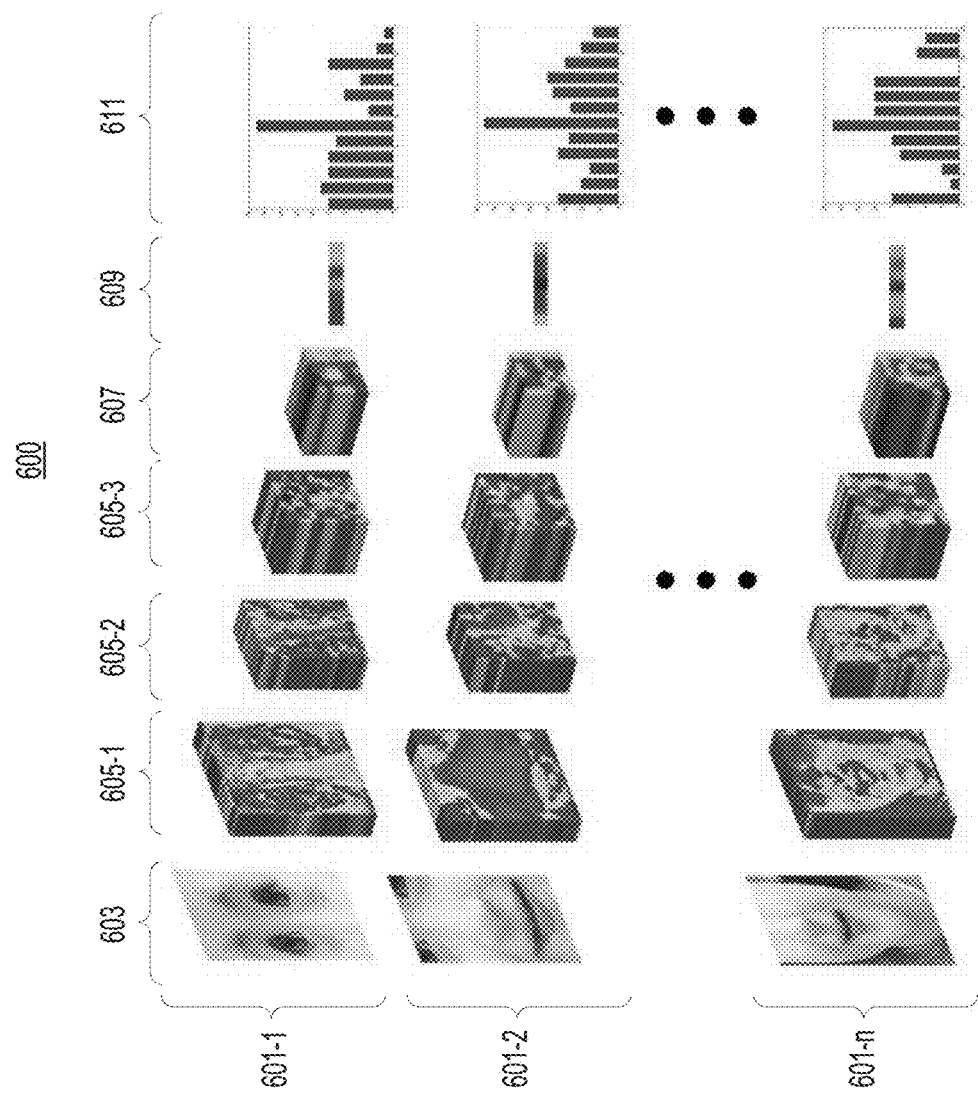
FIG. 6 illustrates an exemplary pipeline for comparing patient phenotypes that may be used for implementing the disclosed embodiments.

FIG. 6 illustrates an exemplary pipeline 600 that one or more processors (e.g., processor 410 of device 400 of FIG. 4) may be configured to implement. For example, as discussed above, processor 410 may be configured to implement pipeline 600 by executing software or firmware stored in memory device 420, or may be configured to implement pipeline 600 using dedicated hardware or one or more ASICs.

As depicted in FIG. 6, an image of an external soft tissue may be transformed into electronic numerical information. For example, the image may be divided into n regions of interest such that cropped portions 603 are all generated. The regions of interest may comprise predetermined regions and/or regions identified as including one or more primary portions of the tissue, such as eyes, nose, and mouth if the tissue comprises a face. Cropped portions 603 may be normalized to a fixed size for input into one or more corresponding neural networks 601-1, 601-2, . . . 601-n.

For example, the cropped portions 603 may be input to one or more convolutional layers, e.g., layers 605-1, 605-2, and 605-3, whose outputs are then pooled using max pooling 607. One of more additional convolutional layers (not shown) coupled with one or more pooling steps may be implemented. In some embodiments, average pooling 609 or any other function that combines any amount of the layers in the network into a single descriptor vector may comprise the feature used by comparator 507. In other embodiments, one or more normalization functions, such as softmax function 611, may normalize the feature vectors output by the average pooling 609, e.g., by normalizing the vectors such that they sum to 1. Additionally or alternatively, a fully connected layer (e.g., with dropout 0.5) may operate on average pooling such that the output of the fully connected layer (which may be normalized afterward) is the feature used by comparator 507.

As may be seen in FIG. 6, each neural network 601-1, 601-2, . . . 601-n may be trained separately from the other neural networks. Accordingly, each neural network may be trained to recognize features on its corresponding region of interest. By using region-based neural networks in lieu of or in addition to neural networks on the entire image of the soft tissue, the resolution of details that may be recognized in the image is increased.

Although not depicted, pipeline 600 may further include a rectified linear unit and/or batch normalization after one or more pooling steps. For example, the rectified linear unit and/or batch normalization may be included after max pooling 607 but not after average pooling 609. Although depicted using three convolutional layers paired with max pooling 607, other structures may be used as pipeline 600, such as two convolutional layers, four convolutional layers, or the like paired with max pooling 607. Although depicted with a structure with one pair of convolutional layers and pooling, other structures may be used as pipeline 200, such as two pairs of convolution layers with pooling, three pairs of convolution layers with pooling, or the like.

Figure 7:
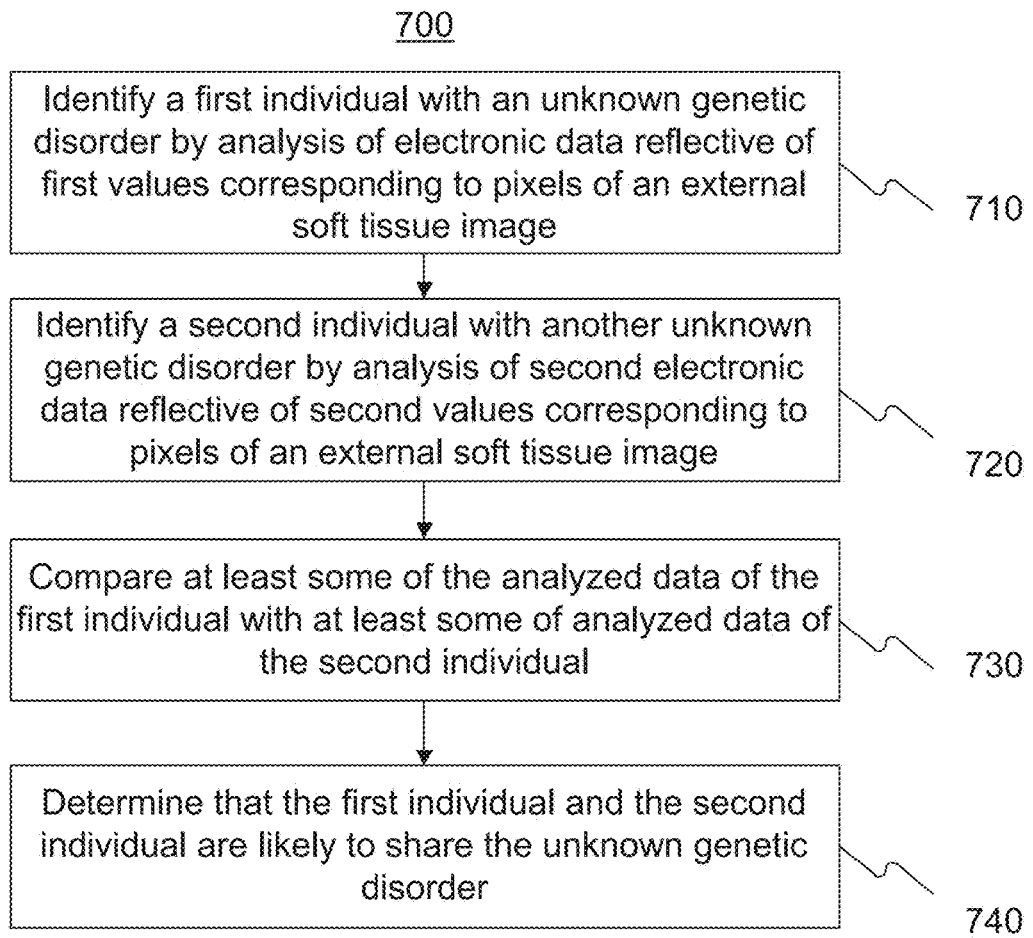
FIG. 7 illustrates example operations that a processor may be configured to perform to match patients having one or more unknown genetic disorders by analyzing images of external soft tissue, in accordance with some of the disclosed embodiments.

FIG. 7 illustrates an exemplary process 700 that one or more processors (e.g., processor 410 of device 400 of FIG. 4) may be configured to perform. For example, as discussed above, processor 410 may be configured to perform process 700 by executing software or firmware stored in memory device 420, or may be configured to perform process 700 using dedicated hardware or one or more ASICs.

Processor 410 may be configured to identify a first individual with an unknown genetic disorder by analysis of first electronic data reflective of first values corresponding to pixels of an external soft tissue image of the first individual (step 710). For example, processor 410 may identify the first individual by receiving the first electronic data as input, by receiving a selection of the first individual from a database of individuals, by extracting the first individual from a database of individuals, or the like.

In some embodiments, the first values may correspond to relationships between at least one group of pixels in the external soft tissue image of the first individual. For example, as explained above, the electronic numerical information may be one or more feature vectors extracted from one or more pooling steps of a neural network. In such embodiments, the electronic numerical information may have been output from one or more convolutional neural networks, which may include one or more convolutional layers and one or more pooling steps. For example, the electronic numerical information may comprise the output of average pooling 219 (or of a fully connected layer and/or a softmax function implemented after average pooling 219) of pipeline 200 of FIG. 2 or of average pooling 607 (or of a fully connected layer and/or a softmax function 611 implemented after average pooling 607) of pipeline 600 of FIG. 6, described above.

Processor 410 may be configured to identify a second individual with another unknown genetic disorder by analysis of second electronic data reflective second values corresponding to second pixels of an external soft tissue image of the second individual (step 720). In some embodiments, the unknown genetic disorder and the another unknown genetic disorder may be determined to be the same disorder. For example, both patients may be matched with a sufficiently high phenotypic similarly score that it may be determined they both have the same genetic disorder that may be unknown to the medical community at the time of diagnosis. The identification of the second individual may be performed similarly to the identification of the first individual, described above. Similar to the first values, in some embodiments, the second values may correspond to relationships between at least one group of pixels in the external soft tissue image of the second individual.

Processor 410 may be configured to compare at least some of the analyzed data of the first individual with at least some of the analyzed data of the second individual (step 730). For example, processor 410 may use any techniques described above with respect to comparator 507 of FIG. 5A and/or comparator 555 of FIG. 5B to perform the comparison. Accordingly, in some embodiments, processor 410 may compare at least some of the analyzed data of the first individual and the analyzed data of the second individual by comparing pixel intensity in corresponding regions of the electronic data for each of the first and second individual. As described above, processor 410 may identify subtle phenotypic similarities between the individuals based on the machine learning engine that are not readily discernible to a treating medical professional when viewing one or more medical images of the patient. In some embodiments, the phenotypic similarities may be discernible only when multiple sources of phenotypic data (e.g., medical images, camera images, annotated images, etc.) are considered by the machine learning engine. In other embodiments, the phenotypic similarities may be discernible only by machine learning engine because the similarities are at a scale that the human eye cannot recognize.

Processor 410 may further be configured to determine that the first individual and the second individual are likely to share the unknown genetic disorder (step 740). For example, as explained above with respect to comparator 555 of FIG. 5B, processor 410 may apply one or more thresholds to the phenotypic similarity score results of the comparison to make the determination.

In some embodiments, determining that the first individual and the second individual are likely to share the unknown genetic disorder occurs without identifying the unknown genetic disorder. For example, as explained above with respect to FIG. 5B, a list of patients having similar representations may be output, the list being indicative of a shared disorder but not explicitly indicating the shared disorder, which may be unrecognized, for example, by the medical community at the time that the patients are matched.

In some embodiments, processor 410 may cluster the first and second individuals into a common group likely to share the unknown genetic disorder. For example, the first and second individuals may be stored together or otherwise linked in a patient database, such as patient database 553 of FIG. 5B. As additional individuals are assigned phenotypic similarity scores above a threshold of similarity with the first and second individuals, these additional individuals may be clustered with the first and second individuals to form a group of individuals likely to share a medical condition.

Method 700 may include further steps. For example, processor 410 may be further configured to receive genetic data from each of the first individual and the second individual. For example, as explained above, the genetic data may comprise sequences of one or more genes of the first individual and the second individual. Accordingly, the genetic data may be textual. Additionally or alternatively, the genetic data may comprise an annotated genome, e.g., with annotations indicating one or more genes of interest. Additionally or alternatively, the genetic data may comprise an encoded genome, e.g., encoded using machine learning such as a neural network that outputs a pathogenic score associated with the genome, one or more feature vectors associated with the genome, or the like.

In such embodiments, based on the received genetic data, processor 410 may determine that the first and second individuals share common genetic anomalies. For example, processor 410 may compare the received genetic data similar to the comparison of the analyzed data at step 730. Processor 410 may therefore make the determination based on the output of both comparisons. For example, processor 410 may derive a list of patients having similar soft tissue representations (e.g., list 559 of FIG. 5B) and a list of patients having similar genetic data (e.g., using similarity scores for the genetic data, similar to the representations). In embodiments where the genetic data includes one or more genes (or genetic variants) of interest, the list of patients having similar genetic data may include patients determined to share at least one of the one or more genes or genetic variants.

In any of the embodiments using genetic data, processor 410 identify the unknown genetic disorder as a new disease based on the common genetic anomalies. For example, processor 410 may output an indicator of a new disorder based on overlap of the lists described above with no corresponding record associating the common genetic anomaly (e.g., shared gene or gene variant) with a disease. In such embodiments, the identification may further use symptoms associated with the patients. For example, processor 410 may output the indicator when no corresponding record associating the common genetic anomaly (e.g., shared gene or gene variant) with one or more shared symptoms.

Method 700 may further use data associated with other individuals. For example, processor 410 may identify a plurality of additional individuals with the unknown genetic disorder by: analysis of additional electronic data reflective of additional values corresponding to additional pixels of additional external soft tissue images of the plurality of additional individuals, and comparison of at least some of the analyzed data for the additional individuals to the analyzed data of at least one of the first and the second individual. Accordingly, as described above with respect to FIG. 5B, more than two patients may be compared. In such embodiments, processor 410 may further cluster the plurality of additional individuals with the first individual and the second individual into a common group likely to share the unknown genetic disorder.

In any of the embodiments described above, processor 410 may recommend a treatment for at least one of the first individual and the second individual based on the determination that the first individual and the second individual are likely to share the same medical condition (e.g., genetic disorder). For example, processor 410 may access a database (e.g., patient database 553 of FIG. 5B) to extract treatments indicated as successful, at least in part, for the second individual. Accordingly, the treatment recommended for the first individual may be a treatment regimen of the second individual corresponding to an improvement in one or more symptoms experienced by the second individual.

Additionally or alternatively, using a patient database as described above (e.g., patient database 553 of FIG. 5B), processor 410 may identify one or more comparable genetic disorders comparable to the unknown genetic disorder based on a comparison of one or more symptoms of at least one of the first and second individuals and one or more symptoms characteristic of the one or more comparable genetic disorders. For example, a list of common symptoms may be determined, as described above, and the list may be compared to known symptoms associated with other genetic disorders. Based on overlaps between the lists of symptoms (e.g., based on a threshold number of overlaps, a threshold percentage of overlap), processor 410 may output the other genetic disorders as comparable. This may be used in lieu of or in addition to the treatment determination described above to determine recommended treatment for at least the first individual.

In an alternative embodiment, processor 410 may identify a first individual with an unknown genetic disorder by analysis of the first electronic data and identify a second individual with a known genetic disorder by analysis of the second electronic data. In such an embodiment, processor 410 may compare at least some of the analyzed data of the first individual with at least some of the analyzed data of the second individual and determine that the first individual is likely to share the known genetic disorder of the second individual based on the comparison. Accordingly, systems of the present disclosure may be used to diagnose known genetic disorders in addition to or in lieu of identifying unknown genetic disorders. In such embodiments, determining that the first individual is likely to share the known genetic disorder may include determining that the unknown genetic disorder is likely within a class defined by a genomic pathway that contains the known genetic disorder. For example, the class defined by the genomic pathway may include a number of genetic disorders that are caused by variants within one or more of the same genes.

Certain features which, for clarity, are described in this specification in the context of separate embodiments, may also be provided in combination in a single embodiment. Conversely, various features which, for brevity, are described in the context of a single embodiment, may also be provided in multiple embodiments separately or in any suitable sub-combination. Moreover, although features may be described above as acting in certain combinations and even initially claimed as such, one or more features from a claimed combination can in some cases be excised from the combination, and the claimed combination may be directed to a subcombination or variation of a subcombination.

Particular embodiments have been described. Other embodiments are within the scope of the following claims.

What is claimed is:

1. An electronic system for performing image processing in connection with phenotypic analysis, the electronic system comprising:
   at least one memory for storing computer-executable instructions; and
   at least one processor configured to execute the stored instructions to:
      receive electronic numerical information corresponding to pixels reflective of at least one external soft tissue image of an individual;
      access geographically dispersed genetic information stored in a database, wherein the geographically dispersed genetic information includes numerical data that correlates anomalies in pixels in soft tissue images of a plurality of geographically dispersed individuals to specific genes or to specific genetic variants;
      compare the electronic numerical information for the individual with the numerical data of the geographically dispersed genetic information stored in a database, to determine at least a likelihood that the individual has at least one pathogenic genetic variant; and
      prioritize, based on the comparison, one or more genetic variants according to a likelihood of pathogenicity.

2. The system of claim 1, wherein prioritizing includes assigning the one or more genetic variants to at least one pathogenicity class.

3. The system of claim 1, wherein the at least one processor is further configured to access phenotypic data associated with the individual and phenotypic data associated with the plurality of geographically dispersed individuals, and wherein the prioritizing is further based on a comparison of the phenotypic data of the individual with the phenotypic data of the geographically dispersed individuals.

4. The system of claim 3, wherein the phenotypic data associated with the individual and the phenotypic data associated with the plurality of geographically dispersed individuals are textual.

5. The system of claim 3, wherein the phenotypic data associated with the individual is received from the individual.

6. The system of claim 3, wherein the phenotypic data associated with the plurality of geographically dispersed individuals is received from the plurality of geographically dispersed individuals.

7. The system of claim 1, wherein the geographically dispersed genetic information includes genetic test information.

8. The system of claim 7, wherein the genetic test information includes one or more medical professional annotations.

9. The system of claim 8, wherein the one or more professional annotations includes words coding for a phenotypic feature.

10. The system of claim 9, wherein the phenotypic feature includes a description of a medical professional observation of an anatomical feature.

11. The system of claim 1, wherein the at least one external soft tissue image of the individual is two-dimensional.

12. The system of claim 1, wherein the electronic numerical information comprises de-identified representations of the at least one external soft tissue image.

13. The system of claim 12, wherein de-identification is performed using one or more convolutional neural networks.

14. A computer-implemented method for performing image processing in connection with phenotypic analysis, the method comprising:
   receiving, with processing circuitry, electronic numerical information corresponding to pixels reflective of at least one external soft tissue image of an individual;
   accessing geographically dispersed genetic information stored in a database, wherein the geographically dispersed genetic information includes numerical data that correlates anomalies in pixels in soft tissue images of a plurality of geographically dispersed individuals to specific genes or to specific genetic variants;
   comparing, with the processing circuitry, the electronic numerical information for the individual with the numerical data of the geographically dispersed genetic information stored in a database, to determine at least a likelihood that the individual has at least one pathogenic genetic variant; and
   prioritizing, with the processing circuitry, based on the comparison, one or more genetic variants according to a likelihood of pathogenicity.

15. The method of claim 14, further comprising:
   accessing phenotypic data associated with the individual and phenotypic data associated with the plurality of geographically dispersed individuals,
   wherein the prioritizing is further based on a comparison of the textual phenotypic data of the individual with the phenotypic data of the geographically dispersed individuals.

16. The method of claim 15, wherein the phenotypic data associated with the individual is received from the individual.

17. The method of claim 15, wherein the phenotypic data associated with the plurality of geographically dispersed individuals is received from the plurality of geographically dispersed individuals.

18. The method of claim 14, wherein the geographically dispersed genetic information includes annotated genetic test information.

19. The method of claim 18, wherein the annotations include words coding for a phenotypic feature.

20. The method of claim 14,
wherein the electronic numerical information comprises de-identified representations of the at least one external soft tissue image, and
the method further comprises de-identifying the at least one external soft tissue image using one or more convolutional neural networks.

21. A non-transitory, computer-readable medium storing instructions for performing image processing in connection with phenotypic analysis, the instructions causing one or more processors to:
receive electronic numerical information corresponding to pixels reflective of at least one external soft tissue image of an individual;
access geographically dispersed genetic information stored in a database, wherein the geographically dispersed genetic information includes numerical data that correlates anomalies in pixels in soft tissue images of a plurality of geographically dispersed individuals to specific genes or to specific genetic variants;
compare the electronic numerical information for the individual with the numerical data of the geographically dispersed genetic information stored in a database, to determine at least a likelihood that the individual has at least one pathogenic genetic variant; and
prioritize, based on the comparison, one or more genetic variants according to a likelihood of pathogenicity.

\* \* \* \* \*